US008563022B2

(12) United States Patent
Decuzzi et al.

(10) Patent No.: US 8,563,022 B2
(45) Date of Patent: Oct. 22, 2013

(54) PARTICLES FOR CELL TARGETING

(75) Inventors: Paolo Decuzzi, Bari (IT); Mauro Ferrari, Houston, TX (US)

(73) Assignees: Board of Regents of the University of Texas System, Austin, TX (US); The Ohio State University Research Foundation, Columbus, OH (US)

( * ) Notice: Subject to any disclaimer, the term of this patent is extended or adjusted under 35 U.S.C. 154(b) by 507 days.

(21) Appl. No.: 11/870,077

(22) Filed: Oct. 10, 2007

(65) Prior Publication Data

US 2008/0102030 A1 May 1, 2008

Related U.S. Application Data

(60) Provisional application No. 60/829,075, filed on Oct. 11, 2006.

(51) Int. Cl.
A01N 25/26 (2006.01)
A01N 25/28 (2006.01)
A61K 49/00 (2006.01)

(52) U.S. Cl.
USPC .......................................... 424/417; 424/9.1

(58) Field of Classification Search
None
See application file for complete search history.

(56) References Cited

U.S. PATENT DOCUMENTS

| 4,520,110 | A | 5/1985 | Stryer et al. |
| 4,888,176 | A | 12/1989 | Langer et al. |
| 4,933,185 | A | 6/1990 | Wheatley et al. |
| 5,010,167 | A | 4/1991 | Ron et al. |
| 6,107,102 | A * | 8/2000 | Ferrari .......................... 436/518 |
| 6,355,270 | B1 | 3/2002 | Ferrari et al. |
| 6,858,184 | B2 | 2/2005 | Perline et al. |
| 7,534,449 | B2 * | 5/2009 | Saltzman et al. ............. 424/417 |
| 2003/0114366 | A1 | 6/2003 | Martin et al. |
| 2005/0053590 | A1 | 3/2005 | Meininger |
| 2005/0095174 | A1 | 5/2005 | Wolf |
| 2006/0105032 | A1 | 5/2006 | Lynch et al. |
| 2008/0311182 | A1 * | 12/2008 | Ferrari et al. ................. 424/450 |

FOREIGN PATENT DOCUMENTS

WO    WO 2006/086257       8/2006
WO    WO 2007/120248 A2   10/2007

OTHER PUBLICATIONS

International Search Report dated Sep. 16, 2008 for International Application No. PCT/US07/81097, 4 pgs.
International Search Report and Written Opinion from counterpart PCT/US2007/081097, mailed Sep. 16, 2008, 14 pages.
Blackwell et al., "Ligand coated nanosphere adhesion to E- and P-selectin under static and flow conditions," Ann. Biomed. Eng., 2001, 29:523-533.

Capo et al,. "Nonspecific binding by macrophages: evaluation of the influence of medium-range electrostatic repulsion and short-range hydrophobic interaction," Immunol. Commun. 1981, 10(1):35-43.
Cohen et al., "Microfabrication of Silicon-Based Nanoporous Particulates for Medical Applications," Biomedical Microdevices, 2003, 5(3):253-259.
Crommelin et al. "Liposomes," Colloidal Drug Delivery Systems, Kreuter, Ed., New York: Marcel Dekker, 1994, 3:73-190.
Dammers et al., "Shear stress depends on vascular territory : comparison between common carotid and brachial artery," J. Appl. Physiol., 2003, 94:485-489.
Decuzzi et al., "Adhesion of Microfabricated Particles on Vascular Endothelium: A Parametric Analysis," Annals of Biomedical Engineering, Jun. 2004, 32(6):793-802.
Decuzzi et al., "A Theoretical Model for the Margination of Particles within Blood Vessels," Annals of Biomedical Engineering, Feb. 2005, 33(2):179-190.
Decuzzi et al., "The adhesive strength of non-spherical particles mediated by specific interactions," Biomaterials, 2006, 27:5307-5314.
Decuzzi et al., "The Effective Dispersion of Nanovectors Within the Tumor Microvasculature," Annals of Biomedical Engineering, Apr. 2006, 34(4):633-641.
Dembo et al., "The reaction-limited kinetics of membrane-to-surface adhesion and detachment," Proc. R. Soc. Lond. B., 1988, 234:55-83.
Duncan R., "The dawning era of polymer therapeutics," Nat. Rev. Drug Discov., May 2003, 2:347-360.
Ferrari, M., "Cancer nanotechnology: opportunities and challenges," Na. Rev. Cancer, Mar. 2005, 5:161-171.
Ferrari, M., "Nanovector therapeutics," Curr. Opin. Chem. Biol., 2005, 9:343-346.
Gavze et al., "Motion of inertial spheroidal particles in a shear flow near a solid wall with special application to aerosol transport in microgravity," J. Fluid Mech., 1998, 371:59-79.
Gbadamosi et al., "PEGylation of microspheres generates a heterogeneous population of particles with differential surface characteristic and biological performance," FEBS Lett., 2002, 532(3):338-344.
Goldman et al., "Slow viscous motion of a sphere parallel to a plane wall. II. Couette flow," Chem. Eng. Sci., 1967, 22:653-660.
Hashizume et al, "Openings between defective endothelial cells explain tumor vessel leakiness," American Journal of Pathology, Apr. 2000, 156(4):1363-1380.
Hsu et al., "The motion of a rigid body in viscous fluid bounded by a plane wall," J. Fluid Mech., 1989, 207:29-72.
Illing et al., "Investigation on particle self-assembly in solid lipid-based colloidal drug carrier systems," Pharm. Res., Apr. 2004, 21(4):592-597.

(Continued)

Primary Examiner — Robert M Kelly
(74) Attorney, Agent, or Firm — Winstead PC

(57) ABSTRACT

Provided is a composition that includes oblate spheroidal particles comprising an active agent, such as a therapeutic or imaging agent, and a method for treating or monitoring a physiological condition, such as a disease, by administering the composition to a subject in need thereof. Also provided are methods for making particles that have a volume that can enhance the particles' adhesion to a target site in a subject's body for a pre-selected shape of the particles and methods for making particles that have a shape that can enhance particles' adhesion to a target site in a subject's body for a pre-selected volume of the particles.

4 Claims, 3 Drawing Sheets

(56) References Cited

OTHER PUBLICATIONS

Figure 1:
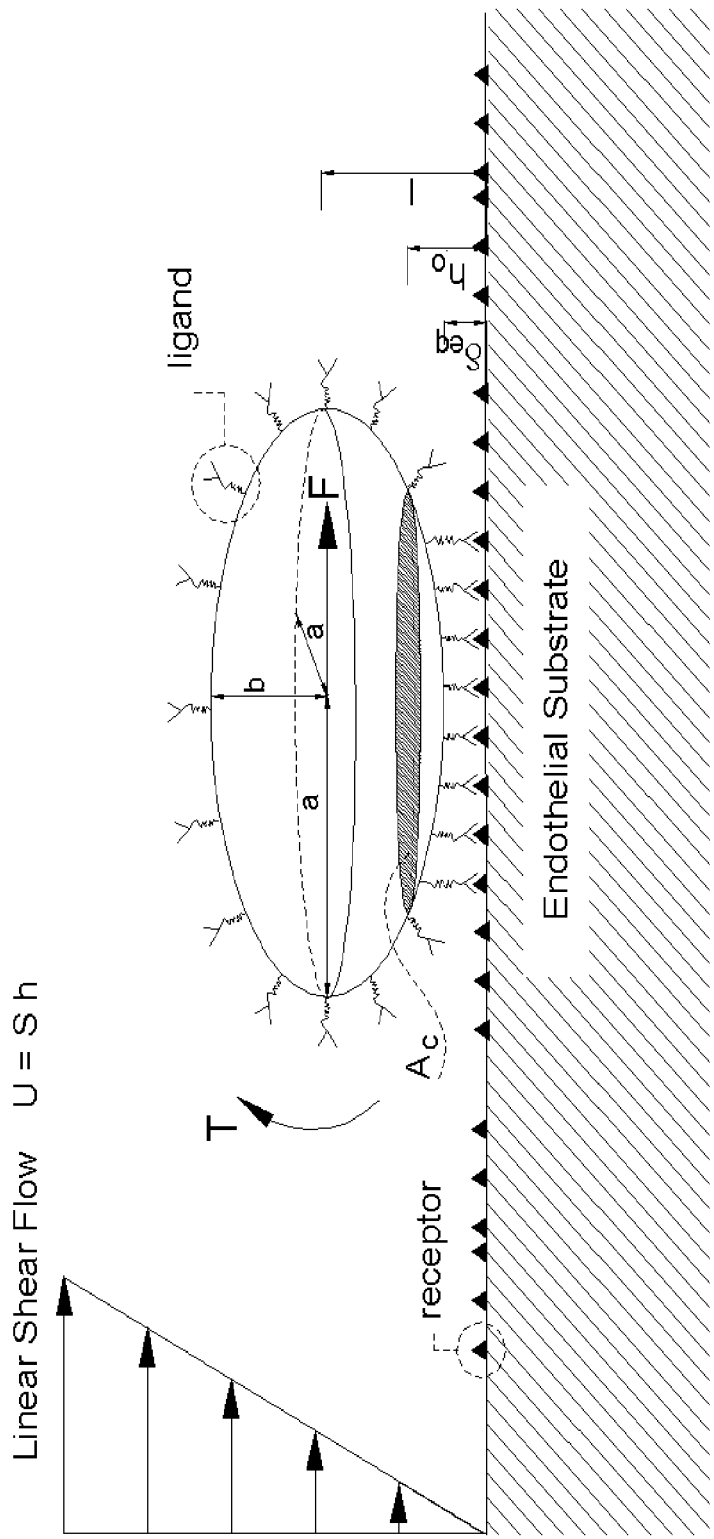

Jain, R.K., "Delivery of molecular and cellular medicine to solid tumors," Advanced Drug Delivery Reviews, 2001, 46:149-168.
Kohli et al., "Smart nanotubes for biotechnology," Curr. Pharm. Biotechnol., 2005, 6(1):35-47.
Krasik et al., "A semianalytic model of leukocyte rolling," Biophys. J., Nov. 2004, 87:2919-2930.
Krasnici et al., "Effect of the surface charge of liposomes on their uptake by angiogenic tumor vessels," Int. J. Cancer., 2003, 105(4):561-567.
LaVan et al., "Small-scale systems for in vivo drug delivery," Nat. Biotechnol., Oct. 2003, 21(10):1184-1191.
McQuarrie, D.A., "Kinetics of small systems," J. Chem. Eng. Phys., Jan. 15, 1963; 38(2):433-435.
Mege et al., "Use of cell contour analysis to evaluate the affinity between macrophages and glutaraldehyde-treated erythrocytes," Biophys. J., Aug. 1987, 52(2):177-186.
Mollica et al., "A model for temporal heterogeneities of tumor blood flow," Microvascular Research, 2003, 65:56-60.
Neri et al., "Tumor vascular targeting," Nat. Cancer Rev., Jun. 2005, 5:436-446.
Netti et al., "Role of extracellular matrix assembly in interstitial transport in solid tumors," Cancer Research, May 1, 2000, 60:2497-2503.
Paik et al., "Micromachining of mesoporous oxide films for microelectromechanical system structures," J. Mater. Res., Aug. 2002, 17(8):2121-2129.
Panes et al., "Regional differences in constitutive and induced ICAM-1 expression in vivo," Am. J. Physiol., 1995; 269(6Pt2):H1955-1964.
Pierres et al., "Diffusion of microspheres in shear flow near a wall: use to measure binding rates between attached molecules," Biophys. J., Jul. 2001, 81:25-42.
Piper et al., "Determining force dependence of two-dimensional receptor-ligand binding affinity by centrifugation," Biophys. J., Jan. 1998, 74:492-513.
Pozrikidis C., "The motion of particles in the Hele-Shaw cell," J. Fluid Mech., 1994, 261:199-222.
Prodan et al., "Low-frequency, low-field dielectric spectroscopy of living cell suspensions," Journal of Applied Physics, Apr. 1, 2004, 95(7):3754-3756.
Rijnaarts et al., "DLVO and steric contributions to bacterial deposition in media of different ionic strengths," Colloids and Surfaces B: Biointerfaces, 1999, 14(1-4):179-195.
Rolland et al., "Direct fabrication and harvesting of monodisperse, shape specific nano-biomaterials," J. Am. Chem. Soc., Mar. 28, 2005, 127(28):10096-10100.
Shinde Patil et al., "Particle diameter influences adhesion under flow," Biophys. J., Apr. 2001, 80:1733-1743.
Subramaniam et al., "Non-spherical bubbles," Nature, Dec. 2005, 438:930.
Taylor, R., Ed., Protein Immobilization Fundamentals and Applications, 1991, 109-110.
Van Dillen et al., "Ion beam shaping of colloidal assemblies," Mater. Today, Jul./Aug. 2004, 40-46.
Weaver et al., "The Effect of Increased Fibrinogen Content on the Viscosity of Blood," Clin. Sci., 1969, 36:1-10.
Wierenga et al., "Aqueous dispersions of colloidal gibbsite platelets; synthesis, characterization and intrinsic viscosity measurements," Colloids and Surfaces A: Physicochemical and Engineering Aspects, 1998, 134(3):359-371.
Yu et al., "Molecular forces between membranes displaying neutral glycosphingolipids: Evidence for carbohydrate attraction," Biochemistry, 1998, 37:1540-1550.

* cited by examiner

PARTICLES FOR CELL TARGETING

CROSS REFERENCE TO RELATED APPLICATIONS

The present application claims the benefit under 35 U.S.C. §119(e) of U.S. provisional patent application No. 60/829,075 "Particles for Cell Targeting" filed Oct. 11, 2006 to Paolo Decuzzi and Mauro Ferrari, which is incorporated herein by reference in its entirety.

FIELD

The present inventions generally relate to the targeted delivery of therapeutic and/or imaging agents and, more specifically, to micro or nanoparticles, methods of making such particles and methods of using such particles for a targeted delivery of therapeutic and/or imaging agents.

BACKGROUND

Micro or nanoparticles with different compositions and chemico-physical properties can be used for delivery of active agents, such as therapeutic or imaging agents, see e.g. LaVan D. A., et al. Small-scale systems for in vivo drug delivery. Nat. Biotechnol. 2003; 21:1184-91; and Ferrari M. Curr. Opin. Chem. Biol. 2005; 9:343-6. Examples of such micro or nanoparticles include nanospheres, where a pay-load, such as drug molecules or imaging agents, is dispersed within a polymer matrix, see e.g. Duncan R. Nat. Rev. Drug Discov. 2003; 2:347-60; multilayered nano/microcapsules and liposomes, where the pay-load is contained in the internal capsule, see e.g. Crommelin D. J. A., Schreier H., *Liposomes*, pp. 73-190, in: *Colloidal drug delivery systems*, Kreuter J., editor, New York: Marcel Dekker, 1994; and nanoporous Si particles, where the pay-load binds to the pores surface, see e.g. Cohen M. H., et al. Biomed. Microdev. 2003; 5:253-9.

One of the advantages of micro or nanoparticles over free molecules administration may be their multifunctionality and engineerability. For example, micro or nanoparticles can carry a high load of therapeutic agent, which can be released with a precise dosage and scheduling, thus improving the efficacy and specificity of the therapy. The micro or nanoparticles can carry both therapeutic and imaging agents, so that the latter can allow monitoring the evolution of a disease or a physiological condition, such as a cancerous tumor, in vivo upon a therapeutic treatment. Surfaces of the micro or nanoparticles can have targeting moieties, such as ligands of different types that can increase the likelihood of specific recognition of the particles by a target site.

To execute its diagnostic and/or therapeutic mission, a micro or nanoparticle has to adhere firmly to one or more cells of a target site, such as a damaged cell. The firm adherence may be particularly important for targeting a vasculature site, as in such a case the adhesive interaction has to counteract the hemodynamic forces exerted over the particle by the flowing blood tending to dislodge the particle away from the surface of the target site, see e.g. Neri, D. and Bicknell, R. (2005) Nat. Rev. Cancer, 5, 436-446. Thus, a need exists to develop micro or nanoparticles with an enhanced adherence to a target site.

SUMMARY

One embodiment of the invention provides a method of treating or monitoring a physiological condition comprising administering to a subject in need thereof a composition comprising oblate spheroidal particles comprising an effective amount of at least one active agent.

Another embodiment of the invention provides a composition comprising oblate spheroidal particles comprising at least one active agent.

In yet another embodiment, a method is provided comprising (A) selecting a target site having a surface, said surface has one or more first moieties; (B) selecting second moieties complementary to the first moieties; (C) selecting a shape defined by one or more shape parameters; (D) determining a volume maximizing an adherence to the target site based on (i) the selected one or more shape parameters; (ii) one or more parameters of interaction between the first moieties and the second moieties; and (iii) a surface density of the first moieties on the targeted site; and (E) fabricating a particle, that has a shape that is substantially the selected shape and a volume, that is substantially the determined volume; and (F) disposing the second moieties on a surface of the particle.

And in yet another embodiment, a method is provided comprising (A) selecting a target site having a surface, said surface has one or more first moieties; (B) selecting a volume; (C) selecting second moieties complementary to said first moiety; (D) determining a shape maximizing an adherence to the target site based on (i) the selected volume; (ii) parameters of interaction between the first moieties and the second moieties; and (iii) a density of the first moiety of the surface on the target site; (E) fabricating a particle, that has a shape, that is substantially the determined shape, and a volume, that is substantially the selected volume; and (F) disposing the second moieties on a surface of the particle.

DRAWINGS

FIG. 1 schematically depicts a spheroidal particle adhered to an endothelial substrate through a ligand-receptor bond.

Figure 2:
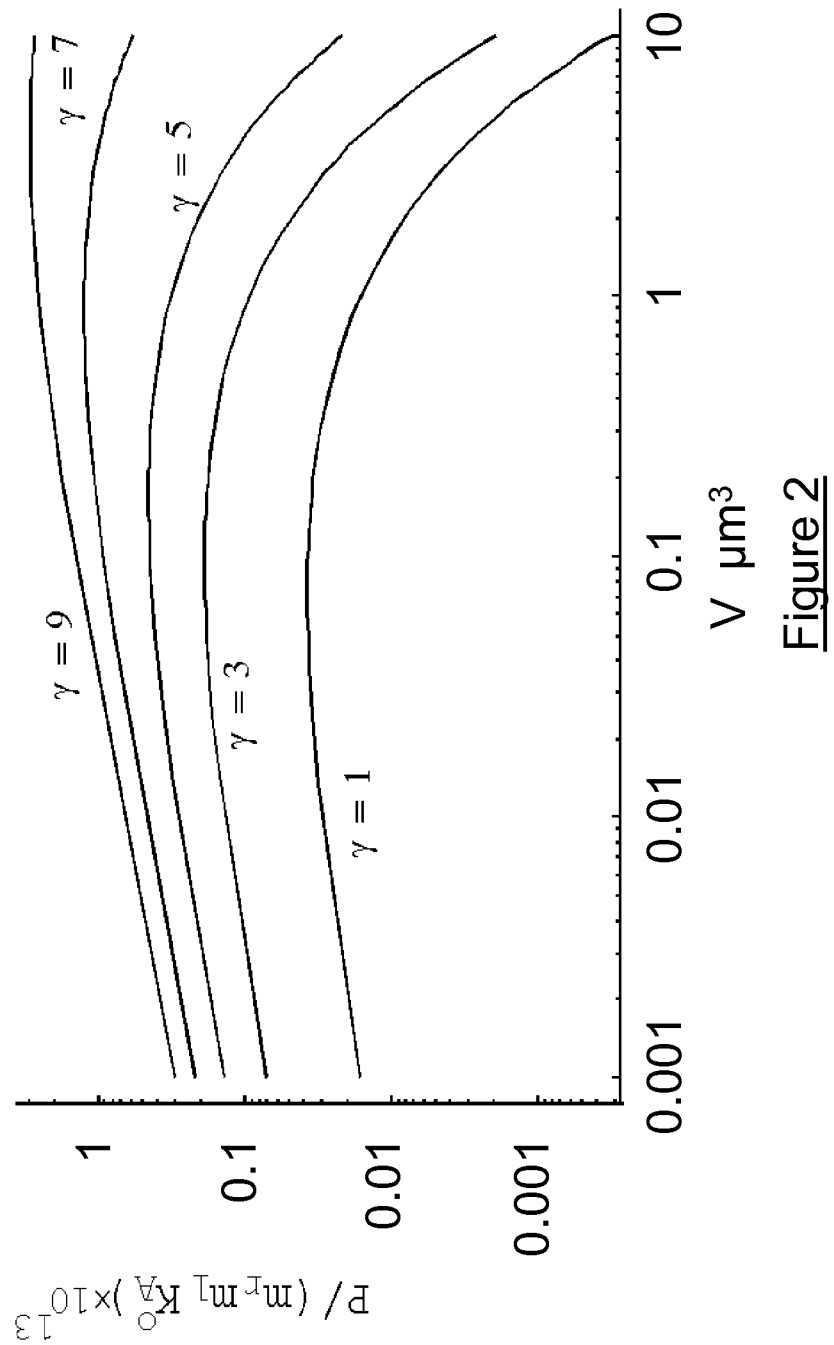

FIG. 2 presents plots of a dimensionless adhesion probability $\tilde{P}_a$ as a function of volume V for several pre-selected values of a spheroidal particle's aspect ratio $\gamma (=1, 3, 5, 7$ and $9)$ for $m_r=10^{14}$ m$^{-2}$; $\mu S=1$ Pa; $\lambda=10^{-10}$ m; $h_0=10^{-8}$ m; $\delta_{eq}=5\times 10^{-9}$ m. A value of volume corresponding to a maximum in $\tilde{P}_a$ is the maximizing volume $V_{opt}$ for a particular pre-selected value of $\gamma$.

Figure 3:
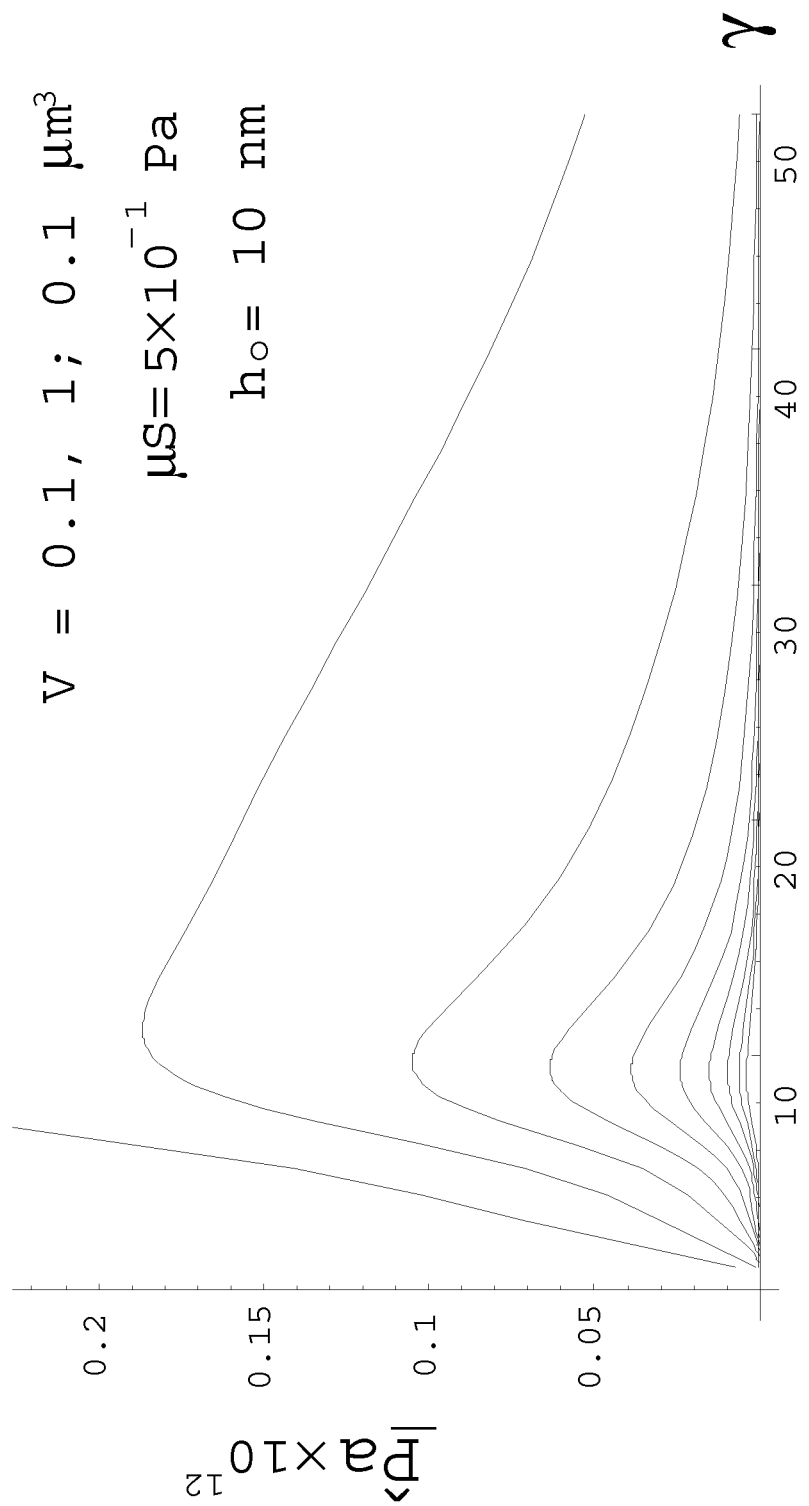

FIG. 3 presents plots of a dimensionless adhesion probability $\tilde{P}_a$ as a function of a spheroidal particle's aspect ratio $\gamma$ for several pre-selected values of volume V ranging from 0.1 to 1 μm$^3$ with a step of 0.10 μm$^3$ for $\mu S=0.5$ Pa; $\lambda=10^{-10}$ m; $h_0=10^{-8}$ m. A value of aspect ratio corresponding to a maximum in $\tilde{P}_a$ is the maximizing aspect ratio $\gamma_{opt}$ for a particular pre-selected value of V.

DETAILED DESCRIPTION

Definitions

Unless otherwise specified "a" or "an" means one or more.

"Microparticle" refers to a particle having a maximum characteristic size from 1 micron to 1000 microns, or, in some embodiments the range is from 1 micron to 100 microns as specifically specified.

"Nanoparticle" refers to a particle having a maximum characteristic size of less than 1 micron.

"Oblate spheroidal particle" means a particle that has substantially a spheroidal shape with an aspect ratio γ more than 1. For the definition of the aspect ratio γ, see below.

"Biodegradable" refers to a material that can dissolve or degrade in a physiological medium or a biocompatible polymeric material that can be degraded under physiological conditions by physiological enzymes and/or chemical conditions.

Overview

The following research articles and patent documents, which are all incorporated herein in their entirety, may be useful for understanding this disclosure:
1) P. Decuzzi and M. Ferrari. The adhesive strength of non-spherical particles mediated by specific interactions, Biomaterials 27 (2006) 5307-5314;
2) P. Decuzzi et al. A Theoretical Model for the Margination of Particles within Blood Vessels, Annals of Biomedical Engineering 33 (2005) 179-190;
3) P. Decuzzi et al. The Effective Dispersion of Nanovectors Within the Tumor Microvasculature, Annals of Biomedical Engineering 34 (2006) 633-641;
4) P. Decuzzi et al. The Adhesion of Microfabricated Particles on Vascular Endothelium: Parametric Analysis, Annals of Biomedical Engineering 32 (2004) 793-802;
5) U.S. patent application Ser. No. 11/836,004 filed Aug. 8, 2007 to Ferrari;
6) PCT application No. PCT/US2006/03986 filed Sep. 27, 2006 to Decuzzi and Ferrari.

The inventors have recognized that particles having an oblate spheroidal shape can adhere to endothelial cells more firmly than spherical particles. Accordingly, embodiments of the invention provide a composition that includes oblate spheroidal particles comprising an active agent, such as a therapeutic or imaging agent, and a method for treating or monitoring a physiological condition, such as a disease, by administering to a subject such as a mammal, preferably human, such a composition. Administering of oblate spheroidal particles may reduce the effective amount of the active agent for treating or monitoring the physiological condition compared to administering of particles having other shapes, such as spherical particles. Although the composition may also contain additional particles that do not have an oblate spheroidal shape, preferably the oblate spheroidal particle constitute at least 20% or at least 30% or at least 40% or at least 50% or at least 60% or at least 70% or at least 80% or at least 90% of the total number of particles in the composition. In some embodiments, substantially all of the particles in the composition are oblate spheroidal particles.

In some embodiments, the average aspect ratio of the oblate spheroidal particles is substantially equal to an adhesion enhancing or maximizing aspect ratio $\gamma_{opt}$ for the average volume of the oblate spheroidal particles. The determination of the adhesion maximizing aspect ratio $\gamma_{opt}$ for a given volume of an oblate spheroidal particle is discussed below.

Also, the average aspect ratio of the oblate spheroidal particles may be such that the maximum characteristic size of the particles a, which is the half-length of the longer axis of the spheroid, is substantially smaller than an average radius r of capillaries at a body site targeted by the composition. Preferably, the maximum characteristic size of the particles is at least 2 times or at least 4 times smaller than the average capillary radius at the targeted body site. The volume V, the maximum characteristic size and the aspect ratio of spheroidal particles are related according to the following equation:

$$\gamma = \frac{4\pi a^3}{3V}.$$

From this equation, one can easily determine $\gamma_{max}$ that satisfies the above relationship between the maximum characteristic size of the particles and the average radius of capillaries at the targeted body site. When $\gamma_{max}$ is smaller than $\gamma_{opt}$ for the average volume of the particles, one can use particles that have an average aspect ratio substantially equal to $\gamma_{max}$.

The physiological condition that can be monitored or treated by oblate spheroidal particles may be any condition, which requires targeted delivery. For example, the physiological condition may be a disease, such as cancer or an inflammation.

The present inventors have also discovered that a micro or nanoparticle having a particular shape can have a volume that may enhance or maximize an adherence of the particle to a particular target site. Also, the inventors have discovered that a micro or nanoparticle having a particular volume may have a shape that may enhance or maximize an adherence of the particle to a particular target site.

Thus, embodiments of the present invention provide methods of making or designing micro or nanoparticles that can have an enhanced adherence to cells of a target site. According to one embodiment, one can (A) select a shape defined by one or more shape parameters, (B) select a target site having a surface that has one or more first moieties on it; (C) select second moieties complementary to the first moieties, (D) determine a volume maximizing adherence to the target site based on (i) the selected shape, (ii) parameters of interaction of the first moieties and the second moieties and (iii) a surface density of the first moieties on the target site; (E) fabricate a particle that has a shape that is substantially the selected shape and a volume that is substantially the determined volume and then (E) dispose the second moieties on the surface of the particle. According to another embodiment, one can (A) select a volume; (B) select a target site having a surface that has one or more first moieties on it; (C) select second moieties complementary to first moieties; (D) determine a shape maximizing an adherence to the target site defined by one or more shape parameters based on (i) the selected volume, (ii) parameters of interaction of the first moieties and the second moieties and (iii) a surface density of the first moieties on the target site; (E) fabricate a particle that has a shape that is substantially the determined shape and a volume that is substantially the selected volume and then (E) dispose the second moieties on the surface of the particle. One can select a particular volume for a particle based on a target load of an active agent desired to be delivered to the target site.

In many embodiments, the selected target site is a vasculature site, such as a coopted vasculature; an angiogenic vasculature or a renormalized vasculature and the first moieties are molecular receptors on the vasculature site. For instance, for a coopted vasculature, the first moieties may be angiopoietin 2 receptors; for an angiogenic vasculature, the first moieties may be vascular endothelial growth factors (VEGF), basic fibroblast growth factors or endothelial markers, such as $\alpha_v\beta_3$ integrins; for renormalized vasculature, the first moieties may be carcinoembionic-related cell adhesion molecules 1 (CEACAM1), endothelin-B receptor (ET-B), vascular endothelial growth factor inhibitors gravin/AKAP12, scaffolding proteins for protein kinase A and protein kinase C.

A surface density on the first moieties may be determined using methods known to those of ordinary skill in the art. For example, when the first moieties are molecular receptors, one can determine their surface density in vivo by using radiolabeled monoclonal antibodies complementary to the receptors as discussed for intercellular adhesion molecule 1 receptors in Panes J., et al. Am. J. Physiol. 1995; 269(6Pt2):H1955-64. Alternatively, a surface density may be determined using fluorescently labeled monoclonal antibodies complementary to the receptors. Such fluorescently labeled monoclonal antibodies may be, for example, antibodies labeled with phycoerythrin as disclosed in U.S. Pat. No. 4,520,110.

The second moieties can be selected to be complementary to the first moieties, i.e. the second moieties are capable to bind the first moiety. For example, for molecular receptors on a targeted vasculature site the second moieties may be antibodies, aptamers or ligands capable to bind the receptors.

A maximum of an adhesion strength of the particle to a target site can correspond to a maximum of a dimensionless adhesion probability $$\tilde{P}_a = A_C \exp\left[-\frac{\lambda f}{k_B T}\right],$$

where $A_C$ is an area of interaction between the micro or nanoparticle and the target site; $\lambda$ is a characteristic length of a bond between the first moieties and the second moieties, e.g. a ligand-receptor bond, f is a force per one first moiety/second moiety pair, e.g. ligand-receptor pair; $k_B$ is the Boltzmann constant; and T is an absolute temperature of the target site expressed in Kelvins. Thus, the adherence maximizing volume can be a volume, for which $\tilde{P}_a$ has a maximum for a preselected shape; while the adherence maximizing shape is a shape, for which $\tilde{P}_a$ has a maximum for a preselected volume.

The following disclosure illustrates determining the adherence maximizing volume and the adherence maximizing shape for a spheroidal micro or nanoparticle, however, it should be understood that similar methods may be applied for a non-spheroidal particle as well.

Spheroidal Particle

FIG. 1 illustrates a spheroidal particle having a ligand surface density $m_l$ adhered to a target site, that is an endothelial substrate having a surface density of receptor molecules $m_r$.

For such a spheroidal particle, selecting one or more shape parameters of the particle means selecting a particular aspect ratio $\gamma = a/b$, where a and b the half lengths of two distinct axes of the spheroidal particle described in Cartesian coordinates as $$\frac{x^2 + y^2}{a^2} + \frac{z^2}{b^2} = 1,$$

where z is the axis of rotational symmetry. The volume of the spheroidal particle is related to the aspect ratio as follows:

$$V = \frac{4}{3}\pi a^3 \gamma^{-1}.$$

The area of interaction $A_C$ can be estimated for a spheroidal particle as $\pi r_0^2$, where $r_0$ is a radius of a circular section of the spheroidal particle located at a separation distance $h_0$ from a surface of the targeted site, where $h_0$ is a maximum distance, at which a specific bond between the first moiety, such as one or more molecular receptors, and the second moiety, such as one or more ligands, can still occur. $\pi r_0^2$ can be estimated as follows:

$$\pi r_0^2 = \pi a^2 \left[1 - \left(1 - \frac{h_0 - \delta_{eq}}{a}\gamma\right)^2\right],$$

where $\delta_{eq}$ is a separation distance between the micro or nanoparticle and a surface of the targeting site, such as an endothelial substrate. FIG. 1 illustrates parameters $A_C$, $r_0$, $\delta_{eq}$ and $h_0$.

The force f per unit ligand-receptor bond may be expressed as a ratio between a total dislodging force $F_{dis}$ and the area of interaction $A_C$ multiplied by the surface density of the first moieties, such as molecular receptors, $m_r$, i.e. $f = F_{dis}/(m_r A_C)$.

The total dislodging force $F_{dis}$ can include two components: one related to a drag force F along a direction of the flow in a blood vessel containing the target site and the other related to a torque T exerted by the blood flow on the particle, see FIG. 1. For a spheroidal particle, the total dislodging force $F_{dis}$ can be written as follows:

$$F_{dis} = F + 2T/r_0 = 6\pi a(a\gamma^{-1} + \delta_{eq})\mu S F^S + 8\pi a^3 \mu S T^S/r_0,$$

where $\mu$ is the dynamic blood viscosity and S is the blood shear rate, $F^S$ and $T^S$ are coefficients, which can be estimated for spheroidal and other non-spherical particles by interpolating the numerical results disclosed in Pozrikidis C. *The motion of particles in the Hele-Shaw cell.* J. Fluid. Mech. 1994; 261:199-222, incorporated herein by reference in its entirety. Thus, for a spheroidal particle, $F^S$ and $T^S$ may be written as $$F^S = 1 + (1.736 - 0.138\gamma + 0.128\gamma^2 + 0.09\gamma^3)e^{-\gamma};$$

$$T^S = 1 + (-20.50 + 46.50\gamma - 35.10\gamma^2 + 8.95\gamma^3)e^{-\gamma}.$$

For a spheroidal particle, a dimensionless adhesion probability may be written as follows:

$$\tilde{P}_a = \pi r_0^2 \exp\left[-\frac{\lambda}{k_B T}\left[6(a\gamma^{-1} + \delta_{eq})F^S + 8\frac{a^2}{r_0}T^S\right]\frac{a}{r_0^2}\frac{\mu S}{m_r}\right].$$

To determine the adherence maximizing volume $V_{opt}$ for a pre-selected $\gamma$, one can differentiate $\tilde{P}_a$ with respect to a and find $a_{opt}$ that sets the first derivative of $\tilde{P}_a$ with respect to a equal to 0 using, for example, numerical or graphical methods. The volume $V_{opt}$ is related to $a_{opt}$ as follows:

$$V_{opt} = \frac{4}{3}\pi a_{opt}^3 \gamma^{-1}.$$

Similarly, to determine the adherence maximizing parameter $\gamma_{opt}$, one can differentiate $\tilde{P}_a$ with respect to $\gamma$ and find $\gamma_{opt}$ that sets the first derivative of $\tilde{P}_a$ with respect to $\gamma$ equal to 0 using, for example, numerical or graphical methods.

FIG. 2 presents plots of a dimensionless adhesion probability $\tilde{P}_a$ as a function of volume V for several preselected values of a spheroidal particle's aspect ratio $\gamma$ (=1, 3, 5, 7 and 9) for $m_r = 10^{14}$ m$^{-2}$; $\mu S = 1$ Pa; $\lambda = 10^{-10}$ m; $h_0 = 10^{-8}$ m; $\delta_{eq} = 5 \times 10^{-9}$ m. A value of volume corresponding to a maximum in $\tilde{P}_a$ is the adherence maximizing volume $V_{opt}$ for a particular pre-selected value of $\gamma$.

FIG. 3 presents plots of a dimensionless adhesion probability $\tilde{P}_a$ as a function of a spheroidal particle's aspect ratio $\gamma$ for several pre-selected values of volume V ranging from 0.1 to 1 μm$^3$ with a step of 0.1 μm$^3$ for $\mu S = 0.5$ Pa; $\lambda = 10^{-10}$ m; $h_0 = 10^{-8}$ m. A value of aspect ratio corresponding to a maximum in $\tilde{P}_a$ is the adherence maximizing aspect ratio $\gamma_{opt}$ for a particular pre-selected value of V.

One can determine numerical values of $V_{opt}$ or $\gamma_{opt}$ prior to fabricating of the particle as all the parameters in the expression $\tilde{P}_a$ based on the selected target site and its properties and parameters of interaction between the first moieties and the second moieties.

For example, for the blood viscosity $\mu$ one can use an average value of $10^{-3}$ Pa s for a human or alternatively one can determine a value of the blood viscosity experimentally from plasma viscosity determined with a glass capillary viscometer, hematocrit and mean wall share rate as disclosed in Weaver J. P. et al. Clin. Sci. 36: 1-10, 1969 and Dammers R., et al. J. Appl. Physiol. 94:485-489, 2003, which are both incorporated herein by reference in their entirety, while the blood share rate S can be assessed non-invasively in vivo with an ultrasound system as described in Dammers R., et al. J. Appl. Physiol. 94:485-489, 2003. Table 1 provides typical numbers of blood share rate for selected blood vessels in humans

TABLE 1

| Vessel | µS, Pa |
|---|---|
| Aorta | 2.5 |
| Artery | 5 |
| Arteriole | 7.5 |
| Capillary | 10 |
| Venules | 0.2 |
| Vein | 0.5 |
| Vena cava | 1 |

$h_0$, a maximum distance, at which a specific bond between the first moiety, such as a molecular receptor, and the second moiety, such as a ligand, may still occur, may be controlled by, for example, changing a length of a linker part of the second moiety.

$\lambda$, a characteristic length of a bond between the first moiety and the second moiety, can depend on the first moieties on the targeted surface and the selected second moieties. For example, when the first moiety is a molecular receptor and the second moiety is a ligand, $\lambda$ can be defined as in Dembo, M., D. C. Torney, K. Saxaman, and D. Hammer. 1988. The reaction-limited kinetics of membrane-to-surface adhesion and detachment. Proc. R. Soc. Lond. B. 234:55-83, which is incorporated herein by reference in its entirety. For typical receptor-ligand pairs, $\lambda$ can be around 1 Å.

$\delta_{eq}$, a separation distance between the micro or nanoparticle and a surface of the target site, such as an endothelial substrate in FIG. 1, can be obtained by solving the following equation with respect to $\delta$ using, for example, numerical or graphical methods:

$$\frac{Aa^2}{k_B T 12 \pi \delta} + \frac{64 \rho_\infty a^2}{\kappa} z_v z_c e^{-\kappa \delta} - 36 \Gamma a^2 e^{-\delta/R_g} = 0.$$

In the above equation, A is a Hamacker constant, which may be estimated using the following formula:

$$A \approx \frac{3}{4} k_B T \left( \frac{\varepsilon_1 - \varepsilon_3}{\varepsilon_1 + \varepsilon_3} \right) \left( \frac{\varepsilon_2 - \varepsilon_3}{\varepsilon_2 + \varepsilon_3} \right) + \frac{3h}{4\pi} \int_{v_1}^{\infty} \left( \frac{\varepsilon_1(iv) - \varepsilon_3(iv)}{\varepsilon_1(iv) + \varepsilon_3(iv)} \right) \left( \frac{\varepsilon_2(iv) - \varepsilon_3(iv)}{\varepsilon_2(iv) + \varepsilon_3(iv)} \right) dv,$$

where $\in_1$, $\in_2$ and $\in_3$ are static (DC) dielectric constants of the particle, endothelial cells and the liquid component of the blood (plasma), respectively; $\in_1(iv)$, $\in_2(iv)$ and $\in_3(iv)$ are values dielectric functions at imaginary frequencies for the particle, endothelial cells and the liquid component of the blood (plasma), respectively; $v_1 = 2\pi k_B T/h$, h is Planck's constant. The dielectric functions and constants can be evaluated using dielectric spectroscopy as disclosed in C. Prodan, F. Mayo, J. R. Claycomb, and J. H. Miller, Jr., M. J. Benedik, *Low-frequency, low-field dielectric spectroscopy of living cell suspensions*, Journal of Applied Physics—Apr. 1, 2004—Volume 95, Issue 7, pp. 3754-3756, which is incorporated herein by reference in its entirety. A typical value for the Hamaker constant in liquids is around $10^{-20}$ Joules, see e.g. Israelachvili, J. 1992, Intermolecular and Surface Forces, 2nd ed. Academic Press, New York.

$\rho_\infty$ is the ionic concentration of blood. A typical value for the ionic concentration for blood can be around 150 mM, see, for example, Ganong, W. F. Review of Medical Physiology, 21st ed. New York: Lange Medical Books/McGraw-Hill Medical Publishing Division, 2003.

$\kappa^{-1}$ is the Debye length, i.e. a length over, which mobile charge carriers (e.g. electrons) can screen out electric fields. Generally, in an electrolyte, such as blood, the Debye length may be determined using the following formula:

$$\kappa^{-1} = \sqrt{\frac{\varepsilon_0 \varepsilon_r k_B T}{2 N_A e^2 I}},$$

where $\in_0$ is the permittivity of free space, $\in_r$ is a dielectric constant of the electrolyte, $k_B$ is Boltzmann's constant, T is the absolute temperature, e is the charge on an electron, I is the ionic strength of the electrolyte, $N_A$ is Avogadro's Number. For blood, the Debye length can be around 0.8 nm.

$\Gamma$ is the number of polymer chains per unit area. $\Gamma = s^{-2}$, where s is the mean separation distance s between two adjacent chains on the surface of the nanoparticle. The separation distance s depends on the size of the functional groups at the nanoparticle surface and on the size of the polymer chains (molecular weight) conjugated to the functional groups. The separation distance s may be estimated by citofluorimetric exams, see for example Jacob N. Israelachvili, Intermolecular and Surface Forces, Second Edition: With Applications to Colloidal and Biological Systems, Academic Press; II Edition, 1992.

$R_g$ is a radius of gyration of a polymer, such as a ligand. $R_g$ can be related to the number N of repeat units of the polymer forming a chain of the polymer and the effective length of the repeat unit, l. $R_g$ can also depend on the polymer's solvent. For an ideal solution, i.e. a solution, where the interaction (attractive repulsive) between the repeat units of the polymers is negligible, $$R_g = l \sqrt{\frac{N}{6}}.$$

For a "good" solvent, i.e. a solvent with repulsion between the segments, $R_g = lN^{3/5}$; for a "bad" solvent, i.e. a solvent with attractive interaction between the repeat units, $R_g = lN^{1/3}$, see e.g. Jacob N. Israelachvili, *Intermolecular and Surface Force: With Applications to Colloidal and Biological Systems*, Academic Press; Second Edition, 1992. The liquid component of blood (plasma) is an aqueous solution and water is a good solvent for PEG polymers.

$z_v$ and $z_c$ are electrostatic surface potentials at the surface of the particle and at the surface of the target site respectively. $\in_v$ and $\in_c$ can be estimated using Zetasizer™ Nano series instrument from Malvern Instruments, Worcestershire United Kingdom.

Fabrication

Upon determining the adherence maximizing volume for the pre-selected shape, one can fabricate the particle that has a volume that is substantially the adherence maximizing volume and a shape substantially determined by the one or more pre-selected shape parameters. Similarly upon determining the adherence maximizing shape parameter for the pre-selected volume, one can fabricate the particle that has a volume that is substantially the pre-selected volume and a shape substantially determined by the adherence maximizing shape parameter. The fabricated particle can be then decorated with the second moieties.

For the volume, the term "substantially" means that the volume is as close to the pre-selected or the determined volume as the particular fabrication method permits. Thus, the fabricated volume may be within ±30% or within ±20% or within ±10% or within ±5% or within ±3% of the pre-selected volume or the determined volume.

For the shape, the term "substantially" means that the shape is as close to the pre-selected or the determined shape as the particular fabrication process permits. For example, for spheroidal particles, the fabricated aspect ratio can be within ±30% or within ±20% or within ±10% or within ±5% or within ±3% or within ±1% of the pre-selected or determined aspect ratio.

The particle(s) can be fabricated by any of a variety of methods. In some embodiments, the particle(s) are fabricated as detailed in van Dillen T., van Blaaderen A., Polman A. *Ion beam shaping of colloidal assemblies*. Mater. Today 2004:40-6, incorporated herein by reference in its entirety. This technique can be used for transforming spherical silica particles into oblate spheroids and ellipsoids.

In some embodiments, the particle(s) is fabricated as a gas bubble or a liquid drop that can exist in a stable non-spherical shape as disclosed in Subramaniam A. B., Abkarian M., Mahadevan L., Stone H. A. *Nonspherical bubbles*. Nature 2005; 438:930, incorporated herein by reference in its entirety.

In some embodiments, the particle(s) are fabricated using particle replication in non-wetting templates (PRINT) technique detailed, for example, in Rolland J. P., Maynor B. W., Euliss L. E., Exner A. E., Denison G. M., DeSimone J. *Direct fabrication and harvesting of monodisperse, shape specific nano-biomaterials*. J. Am. Chem. Soc. 2005; 127:10096-100, incorporated herein by reference in its entirety. This technique is extremely versatile and flexible and enables fabrication of particles with a simultaneous control over shape, size, composition, cargo and surface structure.

In some embodiments, the particle(s) is fabricated by a top-down microfabrication or nanofabrication methods, such as photolithography, electron beam lithography, X-ray lithography, deep UV lithography or nanoprint lithography. One potential advantage of using the top-down fabrication methods is that such methods make possible a scaled up production of particles that are uniform in dimensions.

Upon the fabrication, the second moieties, such as ligands, may be disposed on the surface of the particle. For example, ligands may be chemically linked to appropriate reactive groups on the surface of the particle. Protein ligands may be linked to amino- and thiol-reactive groups under conditions effective to form thioether or amide bonds respectively. Methods for attaching antibody or other polymer binding agents to an inorganic or polymeric support are detailed, for example, in Taylor, R., Ed., Protein Immobilization Fundamentals and Applications, pp. 109110 (1991). Preferably, the second moieties are disposed in such a way that their surface density is higher than the surface density of the first moieties on the target site.

In some embodiments, the fabricated particle has a body defined by a volume and a shape of the particle and one or more reservoirs inside the body, where one or more active agents may be loaded.

In some embodiments, the particle has one or more channels connecting the reservoir with the surface. In some embodiments, the reservoir and the channels are pores in the body of the particle. In such case, the particle may comprise either a porous or nanoporous material. The pores of the porous or nanoporous material may be controlled to achieve a desired load of the active agent and a desired release rate. The nanoporous material with controllable pore size may be an oxide material, such as $SiO_2$, $Al_2O_3$, or $TiO_2$. Fabrication of nanoporous oxide particles, also known as sol gel particles, is detailed, for example, in Paik J. A. et. al. J. Mater. Res., Vol. 17, August 2002, incorporated herein by reference in its entirety. The nanoporous material with controllable pore size may also be nanoporous silicon. For details of fabrication of nanoporous silicon particles, see Cohen M. H. et. al. Biomedical Microdevices 5:3, 253-259, 2003.

Yet in some embodiments, the particle has no channels at all. Such a particle may comprise, for example, a biodegradable material. For example, the particle may be formed of metals, such as iron, titanium, gold, silver, platinum, copper, and alloys and oxides thereof. The biodegradable material may also be a biodegradable polymer, such as polyorthoesters, polyanhydrides, polyamides, polyalkylcyanoacrylates, polyphosphazenes, and polyesters. Exemplary biodegradable polymers are described, for example, in U.S. Pat. Nos. 4,933,185, 4,888,176, and 5,010,167. Specific examples of such biodegradable polymer materials include poly(lactic acid), polyglycolic acid, polycaprolactone, polyhydroxybutyrate, poly(N-palmitoyl-trans-4-hydroxy-L-proline ester) and poly(DTH carbonate).

In some embodiments, the fabricated particle is an active agent per se.

Loading Active Agent

In some embodiments, methods of the invention further comprise loading particle with an active agent. The particular loading technique may depend on the composition of the particle. For example, one can soak the particles fabricated from a nanoporous material in a solution containing a carrying fluid and the active agent, which may enter pores of the earlier stage particle via capillary action. The carrying fluid may be a liquid that is biologically non-harmful and that is neutral with respect to the active agent. An example of the carrying fluid is phosphate buffer saline (PBS) or a deionized water. To maximize a load of the active agent, one may, for example, use a solution that has a saturated concentration of the active agent.

The solution containing the active agent is degassed prior to the introduction of the particles. Then, the particles are submerged in the degassed solution in a sealed chamber. The particles are subjected to reduced pressure to ensure that trapped air is forced from the pores in the particles. Then the particles are fully immersed in the solution and the pressure in the sealed chamber is elevated slightly above atmospheric to make sure that the solution enters the pores of the particles.

The particles are then be trapped on a filter and dried using one of the three methods described below.

To remove any trapped air within the reservoirs in the submerged particles, the pressure within the chamber is reduced, and then raised slightly above atmospheric pressure.

After filling the solution into the pores of the particles, drying is achieved by one or more of the following three methods. Water is removed by evaporation under reduced pressure in a vacuum chamber, or by passage of a stream of warm air or an inert gas such as nitrogen over the surface particles collected on a filter, or by freeze drying. In the case of freeze drying, a flat heat exchanger is placed in good thermal contact, e.g. directly below, the filter, on which the earlier stage particles have been collected. Refrigerant fluid at temperatures ranging from −20° C. to −60° C., such as Freon, or a cold liquid, such as liquid nitrogen, may be passed through the heat exchanger flowing into port and passing out port in order to freeze any water remaining within the pores. The pressure is then reduced until all the water sublimes.

Active Agent

The active agent is a therapeutic compound or an imaging moiety. The active agent may be any appropriate agent. In some embodiments, the active agent is fabricated as a particle. In some embodiments, the active agent is an agent that can be released from a particle incorporating it. The selection of the active agent depends on the application.

The therapeutic agent may be any physiologically or pharmacologically active substance that can produce a desired biological effect in a targeted site in a subject, such as a mammal or a human. The therapeutic agent may be any inorganic or organic compound, without limitation, including peptides, proteins, nucleic acids, and small molecules, any of which may be characterized or uncharacterized. The therapeutic agent may be in various forms, such as an unchanged molecule, molecular complex, pharmacologically acceptable salt, such as hydrochloride, hydrobromide, sulfate, laurate, palmitate, phosphate, nitrite, nitrate, borate, acetate, maleate, tartrate, oleate, salicylate, and the like. For acidic therapeutic agent, salts of metals, amines or organic cations, for example, quaternary ammonium, may be used. Derivatives of drugs, such as bases, esters and amides may also be used as a therapeutic agents. A therapeutic agent that is water insoluble can be used in a form that is a water soluble derivative thereof, or as a base derivative thereof, which in either instance, or by its delivery, is converted by enzymes, hydrolyzed by the body pH, or by other metabolic processes to the original therapeutically active form.

The therapeutic agent may be a chemotherapeutic agent, an immunosuppressive agent, a cytokine, a cytotoxic agent, a nucleolytic compound, a radioactive isotope, a receptor, or a pro-drug activating enzyme, which may be naturally occurring or produced by synthetic or recombinant methods, or any combination thereof.

Drugs that are affected by classical multidrug resistance, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) can have particular utility as the therapeutic agent.

A cancer chemotherapy agent is a preferred therapeutic agent. Useful cancer chemotherapy drugs include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Useful cancer chemotherapy drugs also include alkylating agents, such as Thiotepa and cyclosphosphamide; alkyl sulfonates, such as Busulfan, Improsulfan and Piposulfan; aziridines, such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitrogen mustards, such as Chlorambucil, Chlomaphazine, Cholophosphamide, Estramustine, Ifosfamide, mechlorethamine, mechlorethamine oxide hydrochloride, Melphalan, Novembiehin, Phenesterine, Prednimustine, Trofosfamide, uracil mustard; nitroureas, such as Cannustine, Chlorozotocin, Fotemustine, Lomustine, Nimustine, and Ranimustine; antibiotics, such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites, such as Methotrexate and 5-fluorouracil (5-FU); folic acid analogues, such as Denopterin, Methotrexate, Pteropterin, and Trimetrexate; purine analogs, such as Fludarabine, 6-mercaptopurine, Thiamiprine, and Thioguanine; pyrimidine analogs, such as Ancitabine, Azacitidine, 6-azauridine, Carmofur, Cytarabine, Dideoxyuridine, Doxifluridine, Enocitabine, Floxuridine, and 5-FU; androgens, such as Calusterone, Dromostanolone Propionate, Epitiostanol, Rnepitiostane, and Testolactone; anti-adrenals such as aminoglutethimide, Mitotane, and Trilostane; folic acid replenisher, such as frolinic acid; aceglatone; aldophosphamide glycoside; aminolevulinic acid; Amsacrine; Bestrabucil; Bisantrene; Edatraxate; Defofamine; Demecolcine; Diaziquone; Elformithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylomithine (DMFO); retinoic acid; Esperamicins; Capecitabine; and pharmaceutically acceptable salts, acids or derivatives of any of the above. Also included are anti-hormonal agents that act to regulate or inhibit hormone action on tumors, such as anti-estrogens, including, for example, Tamoxifen, Raloxifene, aromatase inhibiting 4(5)-imidazoles, 4 Hydroxytamoxifen, Trioxifene, Keoxifene, Onapristone, and Toremifene (Fareston); and anti-androgens, such as Flutamide, Nilutamide, Bicalutamide, Leuprolide, and Goserelin; and pharmaceutically acceptable salts, acids or derivatives of any of the above.

Cytokines may also be used as the therapeutic agent. Examples of such cytokines are lymphokines, monokines, and traditional polypeptide hormones. Included among the cytokines are growth hormones, such as human growth hormone, N-methionyl human growth hormone, and bovine growth hormone; parathyroid hormone; thyroxine; insulin; proinsulin; relaxin; prorelaxin; glycoprotein hormones, such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$ and -$\gamma$; colony stimulating factors (CSFs), such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-$\alpha$ or TNF-$\beta$; and other polypeptide factors, including LIF and kit ligand (KL). As used herein, the term cytokine includes proteins from natural sources or from recombinant cell culture and biologically active equivalents of the native sequence cytokines.

The imaging agent may be any substance that can provide imaging information about a targeted site in a body of an animal, such as a mammal or a human being. The imaging agent may comprise magnetic material, such as iron oxide, for magnetic resonance imaging. For optical imaging, the active agent is, for example, a semiconductor nanocrystal or a quantum dot. For optical coherence tomography imaging, the imaging agent is metal, e.g. gold or silver, nanocage particles. The imaging agent is also an ultrasound contrast agent, such as a micro or nanobubble or iron oxide micro or nanoparticle.

Compositions

Also provided is a composition comprising a plurality of the particles. Such a composition may be a suspension of the particles described above for use in administering a therapeutic or imaging agent to a subject. To form the suspension, the particles can be suspended in an aqueous medium at a selected concentration. The optimal concentration will depend on the characteristics (e.g., solubilization properties) of the particle, type of therapeutic application and mode of administration. For example, compositions for oral administration can be relatively viscous, and may therefore contain a high concentration (e.g., >50%) of the particle. Solutions for bolus injections preferably contain a relatively concentrated suspension of the particles (e.g., 10-50%), but not so concentrated that it has an appreciably higher viscosity than saline (to minimize need for large-bore needles). Solution used for continuous intravenous infusion typically contain a relatively low concentration (e.g., 2-10% suspension) of the particles, due to the relatively large volumes of fluid that are administered.

The particles are suspended in any suitable aqueous carrier vehicle. A suitable pharmaceutical carrier is one that is non-toxic to the recipient at the dosages and concentrations employed and is compatible with other ingredients in the formulation. Examples of suitable carrier vehicles include but are not limited to water, saline, Ringer's solution, dextrose solution, and 5% human serum albumin. Suspensions for use in injectable formulations are preferably isotonic with the subject's blood. Generally, the carrier may contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients.

Prior to administration to a subject, the suspension of particles are sterilized by a suitable sterilization method. Particles fabricated from a heat-stable material may be heat-sterilized, e.g., using an autoclave. Particles fabricated from a non-heat-stable material may be sterilized by passage through a commercially-available sterilization filter, e.g., a 0.2 μm filter. Of course, filtration may be used only in cases where the particles is smaller than the pores of the sterilizing filter.

The particles are administered to a subject in need of therapeutic intervention via any suitable administration method. The particular method employed for a specific application is determined by the attending physician. The particles may be administered by one of the following routes: topical, parenteral, inhalation, oral, vaginal and anal. Intravascular administration, which includes intravenous (i.v.), intramuscular (i.m.) and subcutaneous (s.c.) injection, may be particularly preferred.

Intravascular administration may be either local or systemic. Local intravascular delivery may be used to bring the particles in the vicinity of a known lesion by use of guided catheter system, such as a CAT-scan guided catheter. General injection, such as a bolus i.v. injection or continuous/trickle-feed i.v. infusion are typically systemic. Preferably, the particles are injected into the blood stream and allowed to circulate and localize to their target site.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

ADDITIONAL REFERENCES

1. LaVan D A, McQuire T, Langer R. Small-scale systems for in vivo drug delivery. Nat Biotechnol 2003; 21:1184-91.
2. Ferrari M. Nanovector therapeutics. Curr Opin Chem Biol 2005; 9:343-6.
3. Duncan R. The dawning era of polymer therapeutics. Nat Rev Drug Discov 2003; 2:347-60.
4. Crommelin D J A, Schreier H, Liposomes. In: Kreuter J, editor. Colloidal drug delivery systems. New York: Marcel Dekker.

5. Cohen M H, Melnik K, Boiarski A A, Ferrari M, Martin F J. Microfabrication of silicon-based nanoporous particulates for medical applications. Biomed Microdev 2003; 5:253-9.
6. Ferrari M. Cancer nanotechnology: opportunities and challenges. Nat Rev Cancer 2005; 5:161-71.
7. Neri D, Bicknell R. Tumor vascular targeting. Nat Cancer Rev 2005.
8. Vivek R, Patil S, Campbell C J, Yun Y H, Slack S M, Goetz D J. Particle diameter influences adhesion under flow. Biophys J 2001; 80:1733-43.
9. Blackwell J E, Dagia N M, Dickerson J B, Berg E L, Goetz D J. Ligand coated nanosphere adhesion to E- and P-selectin under static and flow conditions. Ann Biomed Eng 2001; 29:523-33.
10. Pierres A, Benoliel A-M, Zhu C, Bongrand P. Diffusion of microspheres in shear flow near a wall: use to measure binding rates between attached molecules. Biophys J 2001; 81:25-42.
11. Krasik E F, Hammer D A. A semianalytic model of leukocyte rolling. Biophys J 2004; 87:2919-30.
12. Wierenga A M, Lenstra T A J, Philipse A P. Aqueous dispersions of colloidal gibbsite platelets; synthesis, characterization and intrinsic viscosity measurements. Colloids Surf A-Physicochem Eng Aspects 1998; 134(3); 359-71.
13. Illing A, Unruh T, Koch M H. Investigation on particle self-assembly in solid lipid-based colloidal drug carrier systems. Pharm Res 2004; 21:592-7.
14. van Dillen T, van Blaaderen A, Polman A. Ion beam shaping of colloidal assemblies. Mater Today 2004:40-6.
15. Kohli P, Martin C R. Smart nanotubes for biotechnology. Curr Pharm Biotechnol 2005; 6(1):35-47.
16. Subramaniam A B, Abkarian M, Mahadevan L, Stone H A. Non-spherical bubbles. Nature 2005; 438:930.
17. Rolland J P, Maynor B W, Euliss L E, Exner A E, Denison G M, DeSimone J. Direct fabrication and harvesting of monodisperse, shape specific nano-biomaterials. J Am Chem Soc 2005; 127:10096-100.
18. Decuzzi P, Lee S, Bhushan B, Ferrari M. A theoretical model for the margination of particles within blood vessels. Ann Biomed Eng 2005; 33(2); 179-90.
19. Pozrikidis C. The motion of particles in the Hele-Shaw cell. J Fluid Mech 1994; 261:199-222.
20. Goldman A J, Cox R G, Brenner H. Slow viscous motion of a sphere parallel to a plane wall. II. Couette flow. Chem Eng Sci 1967; 22:653.
21. McQuarrie D A. Kinetics of small systems. J Chem Eng Phys 1963; 38:433-5.
22. Piper J W, Swerlick R A, Zhu C. Determining force dependence of two-dimensional receptor-ligand binding affinity by centrifugation. Biophys J 1998; 74:492-513.
23. Shinde Patil V R, Campbell C J, Yun Y H, Slack S M, Goetz D J. Particle diameter influences adhesion under flow. Biophys J 2001; 80:1733-43.
24. Gavze E, Shapiro M. Motion of inertial spheroidal particles in a shear flow near a solid wall with special application to aerosol transport in microgravity. J Fluid Mech 1998; 371:59-79.
25. Jain R. K. 2001. Delivery of molecular and cellular medicine to solid tumors. Advanced Drug Delivery Reviews. 46:149-168.
26. Mollica F., R. K. Rakesh, and P. A. Netti. 2003. A model for temporal heterogeneities of tumor blood flow. Microvascular Research. 65:56-60.
27. Hashizume H., P. Baluk, S. Morikawa, J. W. McLean, G. Thurston, S. Roberge, R. K. Jain, and D. M. McDonald. 2000. Openings between defective endothelial cells explain tumor vessel leakiness. American Journal of Pathology. 156(4):1363-1380.
28. Decuzzi P., F. Causa, and P. A. Netti. 2005. The effective dispersion of nanovectors within the microvasculature. Submitted on the Annals of Biomedical Engineering.
29. Netti, P. A., D. A. Berk, M. A. Swartz, A. J. Grodzinsky, and R. K. Jain. 2000. Role of extracellular matrix assembly in interstitial transport in solid tumors, Cancer Research. 60:2497-2503.
30. Decuzzi, P. S. Lee, M. Decuzzi, and M. Ferrari. 2004. Adhesion of microfabricated particles on vascular endothelium: a parametric analysis, Annals of Biomedical Engineering. 32(6):793-802.
31. Krasnici, S., A. Werner, M. E. Eichhorn, M. Schmitt-Sody, S. A. Pahernik, B. Sauer, M. Schulze, M. Teifel, U. Michaelis, K. Naujoks, and M. Dellian. 2003. Effect of the surface charge of liposomes on their uptake by angiogenic tumor vessels. Int. J. Cancer. 105(4):561-567.
32. Gbadamosi, J. K., A. C. Hunter, and S. M. Moghimi. 2002. PEGylation of microspheres generates a heterogeneous population of particles with differential surface characteristic and biological performance, FEBS Lett. 532(3):338-344.
33. Rijnaarts, H. H. M., Norde, J. Lyklema, and A. Zehnder. 1999. DLVO and steric contributions to bacterial deposition in media of different ionic strengths. Colloids and Surfaces B: Biointerfaces, 14(1-4):179-195.
34. Yu, Z. W., T. L. Calvert, and D. Leckbank. 1998. Molecular forces between membranes displaying neutral glycosphingolipids: Evidence for carbohydrate attraction. Biochemistry. 37: 1540-1550.
35. Capo, C., F. Garrouste, A. M. Benoliel, P. Bongrand, and R. Depieds. 1981. Nonspecific binding by macrophages: evaluation of the influence of medium-range electrostatic repulsion and short-range hydrophobic interaction. Immunol Commun 10:35-43.
36. Israelachvili, J. 1992. Intermolecular and surface forces, $2^{nd}$ ed. Academic Press, New York.
37. Hsu, R., and P. Ganatos. 1989. The motion of a rigid body in viscous fluid bounded by a plane wall. J. Fluid Mech. 207:29-72.
38. Mege, J. L., C. Capo, A. M. Benoliel, and P. Bongrand. 1987. Use of cell contour analysis to evaluate the affinity between macrophages and glutaraldehyde-treated erythrocytes. Biophys J. 52(2):177-86.
39. Ganong, W. F. Review of medical physiology, $21^{st}$ ed. Lange Medical Books/McGraw-Hill Medical Publishing Division, New York.

What is claimed is:

1. A method of designing and fabricating particles having an enhanced adherence to cells of a target site, the method comprising
   (A) selecting a target site having a surface, said surface having one or more first moieties;
   (B) selecting second moieties that are capable of binding to the first moieties;
   (C) selecting a numerical value for a spheroid aspect ratio of a spheroidal particle;
   (D) calculating the numerical value of volume that maximizes the adherence strength of the spheroidal particle to the target site using the following input parameters; (i) the selected numerical value of the spheroid aspect ratio; (ii) the area of interaction $\pi r_0^2$ between the spheroidal particle and the target site, where $r_0$ is the radius of the spheroidal particle; and (iii) the numerical value of the surface density of the first moieties on the target site, wherein the volume of the spheroidal particle (V) is related to the aspect ratio ($\gamma$) as $V=4/3\P a^3\gamma^{-1}$, and $\gamma=a/b$, where a and b represent half-lengths of two axes of the spheroidal particle, and $\gamma\geq 1$;

(E) fabricating the spheroidal particle, that has a spheroid aspect ratio substantially equal to the selected numerical value and a volume that has a numerical value that is substantially equal to the calculated numerical value of the maximizing volume; and (F) disposing the second moieties on a surface of the particle wherein the particles obtained have an enhanced adherence to cells of the target site.

2. The method of claim 1, wherein the target site is a vascular site comprising coopted vasculature, an angiogenic vasculature or a renormalized vasculature.

3. The method of claim 1, wherein said first moieties are selected from the group consisting of angiopoietin 2 receptors, vascular endothelial growth factors, basic fibroblast growth factors, endothelial markers, carcinoembryonic-related cell adhesion molecules 1, endothelin-B receptor, AKAP12, and scaffolding proteins.

4. The method of claim 1, wherein said second moieties comprise ligands, aptamers or antibodies.

* * * * *